US010463269B2

(12) United States Patent
Boleyn et al.

(10) Patent No.: US 10,463,269 B2
(45) Date of Patent: Nov. 5, 2019

(54) SYSTEM AND METHOD FOR MACHINE-LEARNING-BASED ATRIAL FIBRILLATION DETECTION

(71) Applicant: Bardy Diagnostics, Inc., Seattle, WA (US)

(72) Inventors: Rodney Boleyn, Bellevue, WA (US);
Ezra M. Dreisbach, Vashon, WA (US);
Chuck Dulken, Sammamish, WA (US);
Gust H. Bardy, Carnation, WA (US)

(73) Assignee: Bardy Diagnostics, Inc., Seattle, WA (US)

( * ) Notice: Subject to any disclaimer, the term of this patent is extended or adjusted under 35 U.S.C. 154(b) by 0 days.

(21) Appl. No.: 16/200,089

(22) Filed: Nov. 26, 2018

(65) Prior Publication Data

US 2019/0090769 A1 Mar. 28, 2019

Related U.S. Application Data

(63) Continuation-in-part of application No. 14/217,402, filed on Mar. 17, 2014, now Pat. No. 10,165,946,
(Continued)

(51) Int. Cl.
*A61B 5/046* (2006.01)
*A61B 5/00* (2006.01)
(Continued)

(52) U.S. Cl.
CPC ............ *A61B 5/046* (2013.01); *A61B 5/0006* (2013.01); *A61B 5/0022* (2013.01);
(Continued)

(58) Field of Classification Search
None
See application file for complete search history.

(56) References Cited

U.S. PATENT DOCUMENTS 3,215,136 A 11/1965 Holter et al.
3,569,852 A 3/1971 Berkovits
(Continued)

FOREIGN PATENT DOCUMENTS

DE 19955211 5/2001
EP 1859833 11/2007
(Continued)

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).
(Continued)

*Primary Examiner* — Brian T Gedeon
(74) *Attorney, Agent, or Firm* — Patrick J. S. Inouye; Leonid Kisselev

(57) ABSTRACT

A system and method for machine-learning based atrial fibrillation detection are provided. A database is maintained that is operable to maintain a plurality of ECG features and annotated patterns of the features. At least one server is configured to: train a classifier based on the annotated patterns in the database; receive a representation of an ECG signal recorded by an ambulatory monitor recorder during a plurality of temporal windows; detect a plurality of the ECG features in at least some of the portions of the representation falling within each of the temporal windows; use the trained classifier to identify patterns of the ECG features within one or more of the portions of the ECG signal; for each of the portions, calculate a score indicative of whether the portion of the representation within that ECG signal is associated the patient experiencing atrial fibrillation; and take an action based on the score.

18 Claims, 11 Drawing Sheets

Related U.S. Application Data which is a continuation-in-part of application No. 14/082,071, filed on Nov. 15, 2013, now Pat. No. 9,433,367, which is a continuation-in-part of application No. 14/080,717, filed on Nov. 14, 2013, now Pat. No. 9,545,204, and a continuation-in-part of application No. 14/080,725, filed on Nov. 14, 2013, now Pat. No. 9,730,593.

(60) Provisional application No. 61/882,403, filed on Sep. 25, 2013, provisional application No. 62/591,715, filed on Nov. 28, 2017.

(51) Int. Cl.

| | |
|---|---|
| G06N 20/00 | (2019.01) |
| A61B 5/0408 | (2006.01) |
| A61B 5/0404 | (2006.01) |
| A61B 5/04 | (2006.01) |
| A61B 5/0402 | (2006.01) |
| A61B 5/0432 | (2006.01) |
| A61B 5/044 | (2006.01) |
| A61B 5/0452 | (2006.01) |
| G06N 3/04 | (2006.01) |
| G06N 3/08 | (2006.01) |

(52) U.S. Cl.
CPC ............ *A61B 5/0402* (2013.01); *A61B 5/044* (2013.01); *A61B 5/0404* (2013.01); *A61B 5/0408* (2013.01); *A61B 5/04017* (2013.01); *A61B 5/0432* (2013.01); *A61B 5/0452* (2013.01); *A61B 5/04085* (2013.01); *A61B 5/04087* (2013.01); *A61B 5/6823* (2013.01); *A61B 5/6832* (2013.01); *A61B 5/6833* (2013.01); *A61B 5/7203* (2013.01); *A61B 5/7267* (2013.01); *A61B 5/742* (2013.01); *A61B 5/748* (2013.01); *G06N 3/0454* (2013.01); *G06N 3/08* (2013.01); *G06N 20/00* (2019.01); *A61B 2560/0487* (2013.01); *A61B 2562/08* (2013.01)

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |

(56) References Cited

U.S. PATENT DOCUMENTS

| | | |
|---|---|---|
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Massif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |

(56) References Cited

U.S. PATENT DOCUMENTS

| | | |
|---|---|---|
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0054737 A1 | 3/2006 | Richardson |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027339 A1 | 1/2008 | Nagai et al. |
| 2008/0051668 A1 | 2/2008 | Bardy |
| 2008/0058661 A1 | 3/2008 | Bardy |
| 2008/0143080 A1 | 3/2008 | Burr |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0312522 A1 | 12/2008 | Rowlandson et al. |
| 2009/0012412 A1 | 1/2009 | Wesel |
| 2009/0012979 A1 | 1/2009 | Bateni et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bishay et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |

(56) References Cited

U.S. PATENT DOCUMENTS

| | | |
|---|---|---|
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shusterman |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0206977 A1 | 7/2014 | Bahney et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0217691 A1 | 7/2016 | Kadobayashi et al. |
| 2016/0235318 A1 | 8/2016 | Sarkar |
| 2017/0112399 A1 | 4/2017 | Brisben et al. |
| 2017/0156592 A1 | 6/2017 | Fu |
| 2017/0281032 A1 | 10/2017 | Weinberg et al. |
| 2017/0366921 A1 | 12/2017 | Pflugh et al. |
| 2018/0078771 A1 | 3/2018 | Koop et al. |
| 2019/0021671 A1 | 1/2019 | Kumar et al. |
| 2019/0059763 A1* | 2/2019 | Shakur ............... A61B 5/04012 |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 6/2010 |
| WO | 2011047207 | 4/2011 |
| WO | 2012140559 | 10/2012 |
| WO | 2012146957 | 11/2012 |
| WO | 2017072250 | 5/2017 |

OTHER PUBLICATIONS

Alivecor, URL <http://www.businesswire.com/news/home/20121203005545/en/AliveCor%E2%80%99s-Heart-Monitor-Phone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; e1-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid," Technology Review, MIT. (May 1, 2009).

Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

Nike+ Fuel Band, URL <http://www.nike.com/us/en_us/c/nikeplus-fuelband> (Web page cached on Jan. 11, 2013.).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmaker.com/2013/09/polar-loop-firstlook.html> (Sep. 17, 2013).

Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).

Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).

Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Sleepview, URL <http://www.clevemed.com/sleepview/overview.shtml> (Web page cached on Sep. 4, 2013.).

(56) References Cited

OTHER PUBLICATIONS

Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2013.).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society.
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/1.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
https://web.archive.org/web/20130831204020/http://www.biopac.com/research.asp?CatID=37&Main=Software (Aug. 2013).
http://www.gtec.at/Products/Software/g.BSanalyze-Specs-Features (2014).
Adinstruments:ECG Analysis Module for LabChart & PowerLab, 2008.
BIOPAC Systems, Inc. #AS148—Automated ECG Analysis , Mar. 24, 2006.
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].
Pranav Rajpurkar et al. "Cardiologist-Level Arrhythmia Detection with Convolutional Neural Networks," arxiv.org, Cornell University Library, 201 Olin Library Cornell University Ithaca, NY 14853, Jul. 6, 2017 (Jul. 6, 2017), XP080774895.
Pourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural Networks (IJCNN), IEEE, Jul. 24, 2016 (Jul. 24, 2016), pp. 5057-5064, XP032992832, DOI: 10.1109/IJCNN.2016.7727866.
Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.

\* cited by examiner

170

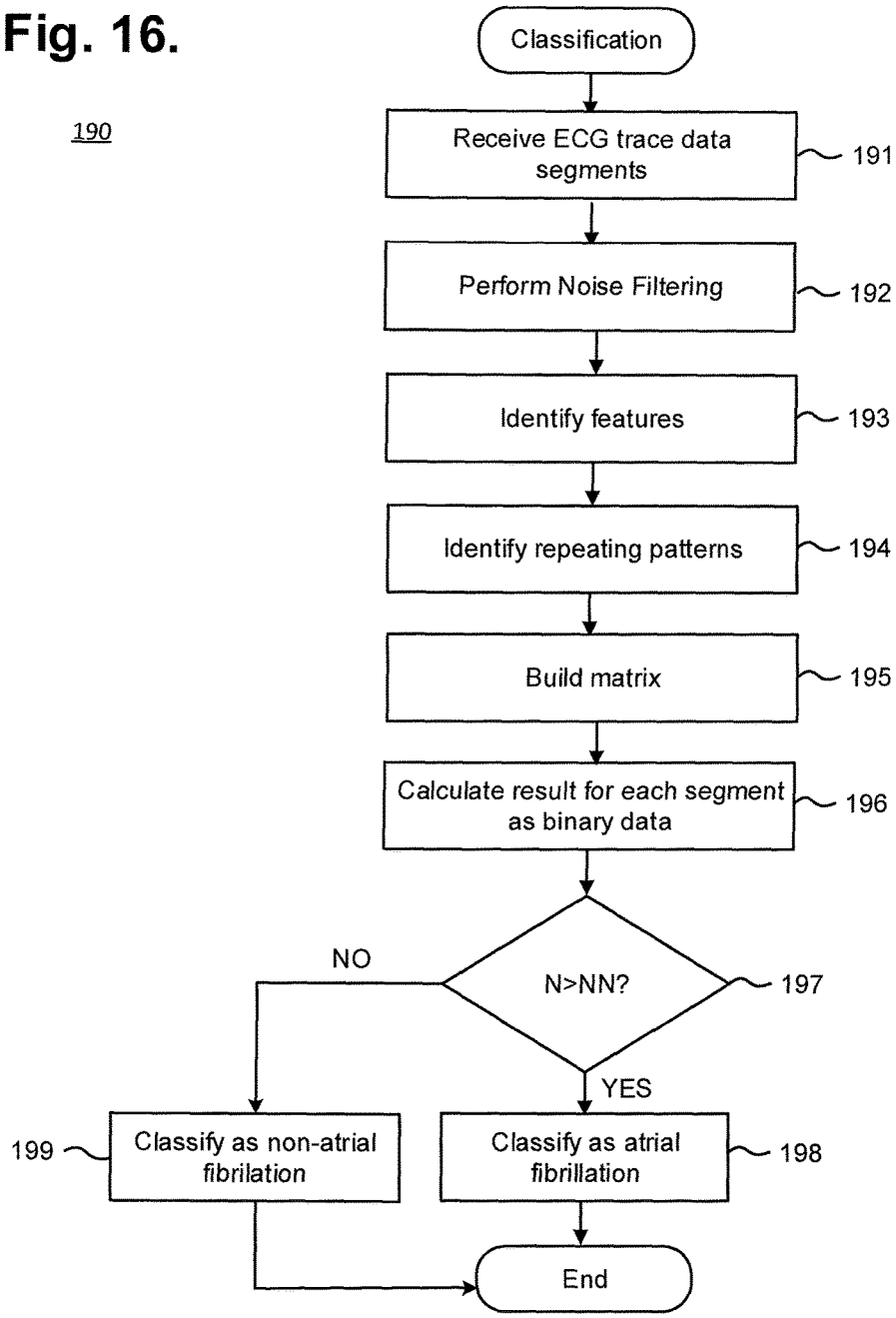

SYSTEM AND METHOD FOR MACHINE-LEARNING-BASED ATRIAL FIBRILLATION DETECTION

CROSS-REFERENCE TO RELATED APPLICATION

This present non-provisional patent application is a continuation-in-part of U.S. Pat. No. 10,165,946, issued Jan. 1, 2019, which is a continuation-in-part of U.S. Pat. No. 9,433,367, issued Sep. 6, 2016; which is a continuation-in-part of U.S. Pat. No. 9,545,204, issued Jan. 17, 2017, and a continuation-in-part of U.S. Pat. No. 9,730,593, issued Aug. 15, 2017; and which further claims priority under 35 U.S.C. § 119(e) to U.S. Provisional Patent application, Ser. No. 61/882,403, filed Sep. 25, 2013, the disclosures of which are incorporated by reference; this non-provisional application also claims priority under 35 U.S.C. § 119(e) to U.S. Provisional Patent application, Ser. No. 62/591,715, filed Nov. 28, 2017, the disclosures of which is incorporated by reference.

FIELD

This application relates in general to electrocardiographic monitoring and, in particular, to a system and method for machine-learning-based atrial fibrillation detection.

BACKGROUND

An electrocardiogram (ECG) records electrical potentials in the heart using a standardized set format 12-lead configuration to record cardiac electrical signals from well-established chest locations. Electrodes are placed on the skin over the anterior thoracic region of the body to the lower right and to the lower left of the sternum, on the left anterior chest, and on the limbs. The recorded cardiac electrical activity, represented by PQRSTU waveforms, can be interpreted to derive heart rate and physiology, where each P-wave represents atrial electrical activity and the QRSTU components represent ventricular electrical activity.

An ECG is a snapshot of heart function, typically recorded over 12 seconds, that can help diagnose rate and regularity of heartbeats, effect of drugs or implantable cardiac devices, and whether a patient has heart disease. ECGs are limited to recording those heart-related aspects present at the time of recording. Thus, an ECG only provides a partial picture and can be insufficient for complete patient diagnosis of many cardiac disorders. Sporadic conditions that may not show up during a spot ECG recording, including fainting or syncope; rhythm disorders, such as tachyarrhythmias and bradyarrhythmias; asystolic episodes; and other cardiac and related disorders, require other means of diagnosis.

Diagnostic efficacy of cardiac rhythm disorders in particular can be improved, when appropriate, through long-term extended ECG monitoring. Recording cardiac physiology over an extended period can be challenging, yet is often essential to enabling a physician to identify events of potential concern. Although a 30-day observation period is considered the "gold standard" of ECG monitoring, achieving 30-day coverage has proven unworkable because conventional ambulatory ECG monitoring systems are arduous to employ, cumbersome to wear, and excessively costly. Nevertheless, if a patient's ECG could be recorded in an ambulatory setting over long periods of time, thereby allowing the patient to engage in activities of daily living, the chances of acquiring meaningful information and capturing an abnormal cardiac rhythm event becomes more likely to be achieved.

For instance, the long-term wear of ECG electrodes is complicated by skin irritation and the inability of conventional ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. These factors adversely affect electrode adhesion and the quality of cardiac signal recordings. Moreover, physical movement and clothing impart compressional, tensile, and torsional forces on electrode contact points decreasing signal quality, especially over long recording times. In addition, an inflexibly fastened ECG electrode is prone to dislodgement that often occurs unbeknownst to the patient, making the ECG recordings worthless. Further, some patients may have skin conditions, such as itching and irritation, aggravated by the wearing of most ECG electrodes. A patient may have to periodically remove or replace electrodes during a long-term monitoring period, whether to replace a dislodged electrode, reestablish better adhesion, alleviate itching or irritation, allow for cleansing of the skin, allow for showering and exercise, or for other purpose. Such replacement or slight alteration in electrode location can interfere with the goal of recording the ECG signal for long periods of time. Finally, such recording devices are often ineffective at recording atrial electrical activity, which is critical in the accurate diagnosis of heart rhythm disorders, because of the use of traditional ECG recording electronics or due to the location of the monitoring electrodes far from the origin of the atrial signal, for instance, the P-wave.

Conventionally, Holter monitors are widely used for long-term extended ECG monitoring, typically, for only 24-48 hours. A typical Holter monitor is a wearable and portable version of an ECG that includes cables for each electrode placed on the skin and a separate battery-powered ECG recorder. Similar to standard in-clinic ECG practice, the cable and electrode combination (or leads) are placed in the anterior thoracic region. The duration of a Holter monitoring recording depends on the sensing and storage capabilities of the monitor, as well as battery life. A "looping" Holter (or event) monitor can operate for a longer period of time by overwriting older ECG tracings, thence "recycling" storage in favor of extended operation, yet at the risk of losing crucial event data. Holter monitors remain cumbersome, expensive and typically for prescriptive use only, which limits their usability. Further, the skill required to properly place the ECG leads on the patient's chest hinders or precludes a patient from replacing or removing the electrodes.

The ZIO XT Patch and ZIO Event Card devices, manufactured by iRhythm Tech., Inc., San Francisco, Calif., are wearable stick-on monitoring devices that are typically worn on the upper left pectoral region to respectively provide continuous and looping ECG recordings. The location is used to simulate surgically implanted monitors. These devices are prescription-only for single patient use. The ZIO XT Patch device is limited to 14-day monitoring, while the ZIO Event Card device's electrodes can be worn for up to 30 days. The ZIO XT Patch device combines electronic recordation components, including battery, and physical electrodes into a unitary assembly that adheres to the skin. The ZIO XT Patch device uses adhesive strong enough to support the weight of both the monitor and the electrodes over an extended period of time. During monitoring, the battery is continually depleted and can potentially limit overall monitoring duration. The ZIO Event Card device is a form of downsized Holter monitor with a recorder component that must be removed during activities that could damage the non-waterproof electronics. These patches have a further limitation because of a small inter-electrode distance coupled to its designed location of application, high on the left chest. The electrical design of the ZIO patch and its location make recording high quality atrial signals (P-waves) difficult, as the location is relatively far from the origin of these low amplitude signals. As well, the location is suboptimal for identification of these signals. Furthermore, this patch is problematical for woman by being placed in a location that may limit signal quality, especially in woman with large breasts or bosoms. Both ZIO devices represent compromises between length of wear and quality of ECG monitoring, especially with respect to ease of long term use, female-friendly fit, and quality of atrial (P-wave) signals.

Personal ambulatory monitoring, both with smartphones or via adjuncts to smartphones, such as with a wirelessly-connected monitor or activity tracker, of varying degrees of sophistication and interoperability, have become increasingly available. For instance, McManus et al., "A Novel Application for the Detection of an Irregular Pulse using an iPhone 4S in Patients with Atrial Fibrillation," Vol. 10(3), pp. 315-319 (March 2013), the disclosure of which is incorporated by reference, discloses obtaining pulsatile time series recordings before and after cardioversion using the digital camera built into a smartphone. An algorithm implemented as an app executed by the smartphone analyzed recorded signals to accurately distinguish pulse recordings during atrial fibrillation from sinus rhythm, although such a smartphone-based approach provides non-continuous observation and would be impracticable for long term physiological monitoring. Further, the smartphone-implemented app does not provide continuous recordings, including the provision of pre-event and post-event context, critical for an accurate medical diagnosis that might trigger a meaningful and serious medical intervention. In addition, a physician would be loath to undertake a surgical or serious drug intervention without confirmatory evidence that the wearer in question was indeed the subject of the presumed rhythm abnormality. Validation of authenticity of the rhythm disorder for a specified patient takes on critical legal and medical importance.

The AliveCor heart monitor, manufactured by AliveCor, Inc., San Francisco, Calif., provides a non-continuous, patient-triggered event monitor, which is worn on the fingertip. Heart rate is sensed over a single lead (comparable to Lead I on a conventional ECG) and recorded by an app running on a smartphone, such as an iOS operating system-based smartphone, such as the iPhone, manufactured by Apple Inc., Cupertino, Calif., or an Android operating system-based smartphone, manufactured and offered by various companies, including Google Inc., Mountain View, Calif.; Samsung Electronics Co., Ltd., Suwon, S. Korea; Motorola Mobility LLC, a subsidiary of Google Inc., Libertyville, Ill.; and LG Electronics Inc., Seoul, S. Korea. The Android operating system is also licensed by Google Inc. The app can send the data recorded by an AliveCor heart monitor from the smartphone to healthcare providers, who ultimately decide whether to use the data for screening or diagnostic purposes. Furthermore, as explained supra with respect to the McManus reference, none of these devices provides the context of the arrhythmia, as well as the medico-legal confirmation that would otherwise allow for a genuine medical intervention.

Similarly, adherents to the so-called "Quantified Self" movement combine wearable sensors and wearable computing to self-track activities of their daily lives. The Fitbit Tracker, manufactured by Fitbit Inc., San Francisco, Calif.; the Jawbone UP, manufactured by Jawbone, San Francisco, Calif.; the Polar Loop, manufactured by Polar Electro, Kempele, Finland; and the Nike+ FuelBand, manufactured by Nike Inc., Beaverton, Oreg., for instance, provide activity trackers worn on the wrist or body with integrated fitness tracking features, such as a heart rate monitor and pedometer to temporally track the number of steps taken each day with an estimation calories burned. The activity tracker can interface with a smartphone or computer to allow a wearer to monitor their progress towards a fitness goal. These activity trackers are accessories to smartphones, including iOS operating system-based smartphones, Android operating system-based smartphones, and Windows Phone operating-system based smartphones, such as manufactured by Microsoft Corporation, Redmond, Wash., to which recorded data must be offloaded for storage and viewing.

The features of activity trackers can also be increasingly found in so-called "smart" watches that combine many of the features of activity trackers with smartphones. Entire product lines are beginning to be offered to provide a range of fitness- and health-tracking solutions. As one example, Samsung Electronics Co., Ltd., offers a line of mobile products with fitness-oriented features, including the Galaxy S5 smartphone, which incorporates a biometric fingerprint reader and heart rate monitor; the Gear 2 smart watch, which also incorporates a heart rate monitor; and the Gear Fit wearable device, which incorporates a heart rate monitor, real time fitness coaching, and activity tracker. The Galaxy S5 smartphone's heart rate monitor is not meant for continuous tracking, while the both the Gear 2 smart watch and Gear Fit wearable device must be paired with a smartphone or computer to offload and view the recorded data.

With all manner of conventional "fitness-oriented" device, whether smartphone, smart watch, or activity tracker, quantified physiology is typically tracked for only the personal use of the wearer. Monitoring can be either continuous or non-continuous. The wearer must take extra steps to route recorded data to a health care provider; thus, with rare exception, the data is not time-correlated to physician-supervised monitoring nor validated. Furthermore, the monitoring is strictly informational and medically-significant events, such as serious cardiac rhythm disorders, including tachyarrhythmias and bradyarrhythmias, while potentially detectable, are neither identified nor acted upon.

In today's medical and legal environment, a mobile device, such as a smartphone, provides information that cannot be translated into data that triggers surgery or drug therapy by a physician. In the case of a smartphone detecting a fast heartbeat, for example, such a detection and the information on the smartphone would neither be identified as truly related to the patient in question or would be deemed sufficient for subjecting a patient to surgery or potentially toxic drug therapy. Thus, such data that is available today is not actionable in a medically therapeutic relevant way. To make such data actionable, one must have recorded data that allows a specific rhythm diagnosis, and a vague recording hinting that something may be wrong with the heart will not suffice. Further, the recorded data must not only identify the heart-related event of concern, but the signals before and after the event, which provides critical medical information for a physician to diagnose the disorder specifically. Finally, the recorded data must be made certifiable, so that the relationship of the recorded data to the patient that the physician is seeing is clear and appropriately identifiable as an event originating in the patient being examined. Establishing this relationship of data-to-patient has become a legally mandatory step in providing medical care, which heretofore has been impracticable insofar as one cannot merely rely upon a smartphone to provide legally sufficient identification of an abnormality with actionable data such that a patient undergoes a serious medical intervention.

Even once ECG monitoring data of sufficient length and quality to serve as a basis for a diagnosis is obtained, further challenges exist in providing an efficient and actionable interpretation of the data. While a physician may personally perform an over-read of the data over the entire length of the monitoring manually, such an over-read consumes a significant amount of time that will slow down delivering any necessary treatment to the patient. While automated interpretation techniques exist, such techniques still have significant limitations in recognizing certain types of cardiac conditions. For example, such techniques may have trouble recognizing atrial fibrillation ("AF"), a condition characterized by a rapid, irregular, beating of the atrium. AF is associated with an increased risk of stroke and heart failure, and is thus an important condition to timely diagnose. Most automated algorithms trying to diagnose AF focus on individual features of the ECG waves, such as particularly focusing on distances between R-waves and comparing them to predefined thresholds. Such an approach ignores other manifestations of AF and may lead to misdiagnosis AF is initially diagnosed by an absence of organized P-waves 11 and confirmed by erratic ventricular rates that manifest in an ECG R-R interval plot as a cloud-like pattern of irregular R-R intervals due to an abnormal conduction of impulses to the ventricles.

Therefore, a need remains for an extended wear continuously recording ECG monitor practicably capable of being worn for a long period of time in both men and women and capable of recording high quality atrial and ventricular signals reliably.

A further need remains for facilities to integrate wider-ranging physiological and "life tracking"-type data into long-term ECG and physiological data monitoring coupled with an onboard ability to cascade into the medical records and to the medical authorities appropriate medical intervention upon detection of a condition of potential medical concern.

A still further need remains for a flexible way to detect atrial fibrillation based on results of an ECG monitoring results that allows to take into account diverse manifestations of atrial fibrillations on an ECG trace.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum, the area most likely to record high quality atrial signals or P-waves. Moreover, the wearable monitor is worn in such a location that is comfortable to woman and allows wear during activity.

In a further embodiment, the wearable monitor can interoperate wirelessly with other wearable physiology monitors and activity sensors and with mobile devices, including so-called "smartphones," as well as with personal computers and tablet or handheld computers, to download monitoring data either in real-time or in batches. Where a wearable physiology monitor, activity sensor, or mobile device worn or held by the patient includes the capability to sense cardiac activity, particularly heart rate, or other physiology, an application executed by the monitor, sensor, or device can trigger the dispatch of a medically-actionable wearable monitor to the patient upon detecting potentially medically-significant events, such as cardiac rhythm disorders, including tachyarrhythmias and bradyarrhythmias. Upon receipt of the wearable monitor, the patient can use the sensor or device, if appropriately equipped with photographic, fingerprint or thumbprint, or other recording features, to physically record the placement and use of the wearable monitor, thereby facilitating the authentication of the data recorded by the wearable monitor. Finally, the monitor recorder can also be equipped with a wireless transceiver to either provide data or other information to, or receive data or other information from, an interfacing wearable physiology monitor, activity sensor, or mobile device for relay to an external system or further device, such as a server, analysis, or for further legal validation of the relationship of the monitor to the patient, or for other purpose.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, particularly hypertrophic or pendulous breasts, would cause chafing, irritation, frustration, and annoyance, leading to low patient compliance and possibly premature removal of the monitoring patch. Furthermore, such conventional patches do not have the electrical design and signal processing that would allow recording of the P-wave, given the close spacing of the bipolar electrodes.

The foregoing aspects enhance ECG monitoring performance and quality, facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis.

Finally, the foregoing aspects as relevant to monitoring are equally applicable to recording other physiological data, such as heart rate, temperature, blood pressure, respiratory rate, blood pressure, blood sugar (with appropriate subcutaneous probe), oxygen saturation, minute ventilation, as well as other measures of body chemistry and physiology.

Further, instances of atrial fibrillation experienced during a cardiac monitoring can be flexibly detected using machine learning. ECG training data is obtained and ECG trace features in the data are identified. Patterns of ECG features in the training data are annotated as either being indicative of a patient having experienced atrial fibrillation or not indicative of a patient having experienced atrial fibrillation. An adaptive atrial fibrillation detector is trained on the annotated patterns and the trained classifier is used to recognize patterns of ECG features indicative of atrial fibrillation in newly-acquired ECG monitoring data. Due to being trained on patterns of ECG features, with more training being possible as more patterns are revealed, the adaptive atrial fibrillation detector can detect more manifestations of atrial fibrillation recorded during an ECG monitoring that would be available through simple use of predefined parameters, such as distances between successive R-waves. Once the atrial fibrillation detection is confirmed by an appropriate medical professional, the detection can serve as a basis for initiating an appropriate treatment of the patient or another action.

In one embodiment, a system and method for machine-learning based atrial fibrillation detection with the aid of a digital computer are provided. A database is maintained that is operable to maintain a plurality of electrocardiography (ECG) features and annotated patterns of the features, at least some of the patterns associated with atrial fibrillation. At least one server is interconnected to the database, the at least one server configured to: train a classifier based on the annotated patterns in the database; receive a representation of an ECG signal recorded by an ambulatory monitor recorder during a plurality of temporal windows; detect a plurality of the ECG features in at least some of the portions of the representation falling within each of the temporal windows; use the trained classifier to identify patterns of the ECG features within one or more of the portions of the ECG signal; for each of the portions, calculate a score indicative of whether the portion of the representation within that ECG signal is associated the patient experiencing atrial fibrillation; and take an action based on the score.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 16 is a flow diagram showing, by way of example, a routine 190 for classification of ECG data for use in the method 170 of FIG. 14 in accordance with one embodiment.

DETAILED DESCRIPTION

Figure 1:
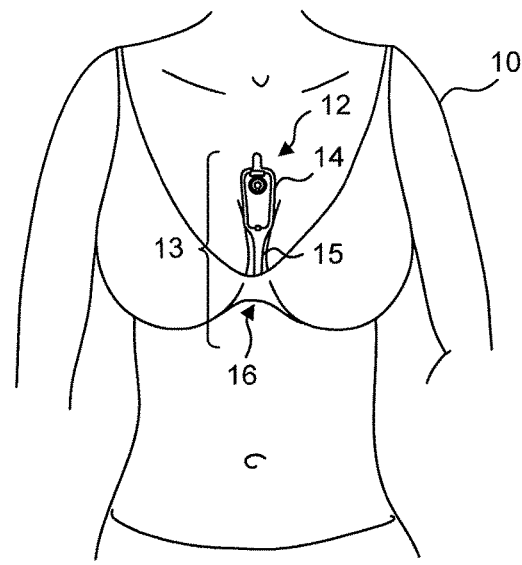
FIGS. 1 and 2 are diagrams showing, by way of examples, an extended wear electrocardiography and physiological sensor monitor respectively fitted to the sternal region of a female patient and a male patient.
Figure 2:
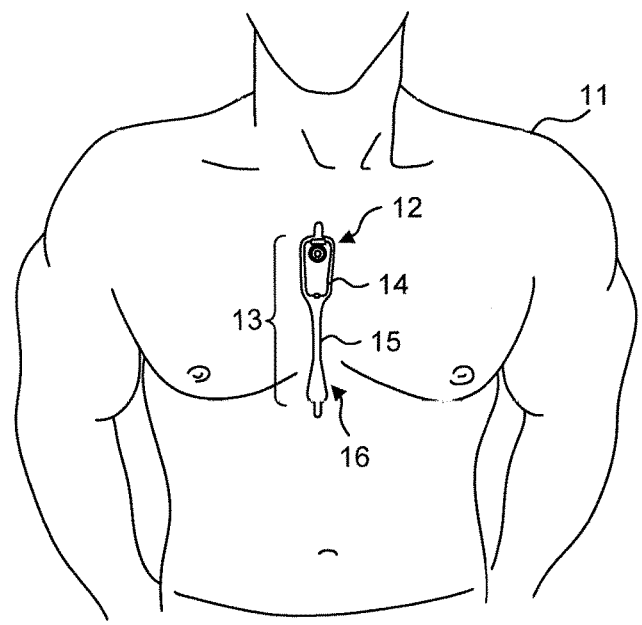

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity, while simultaneously facilitating comfortable long-term wear for many weeks. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the Xiphoid process facilitates sensing of ventricular activity and provides superior recordation of the QRS interval.

Figure 3:
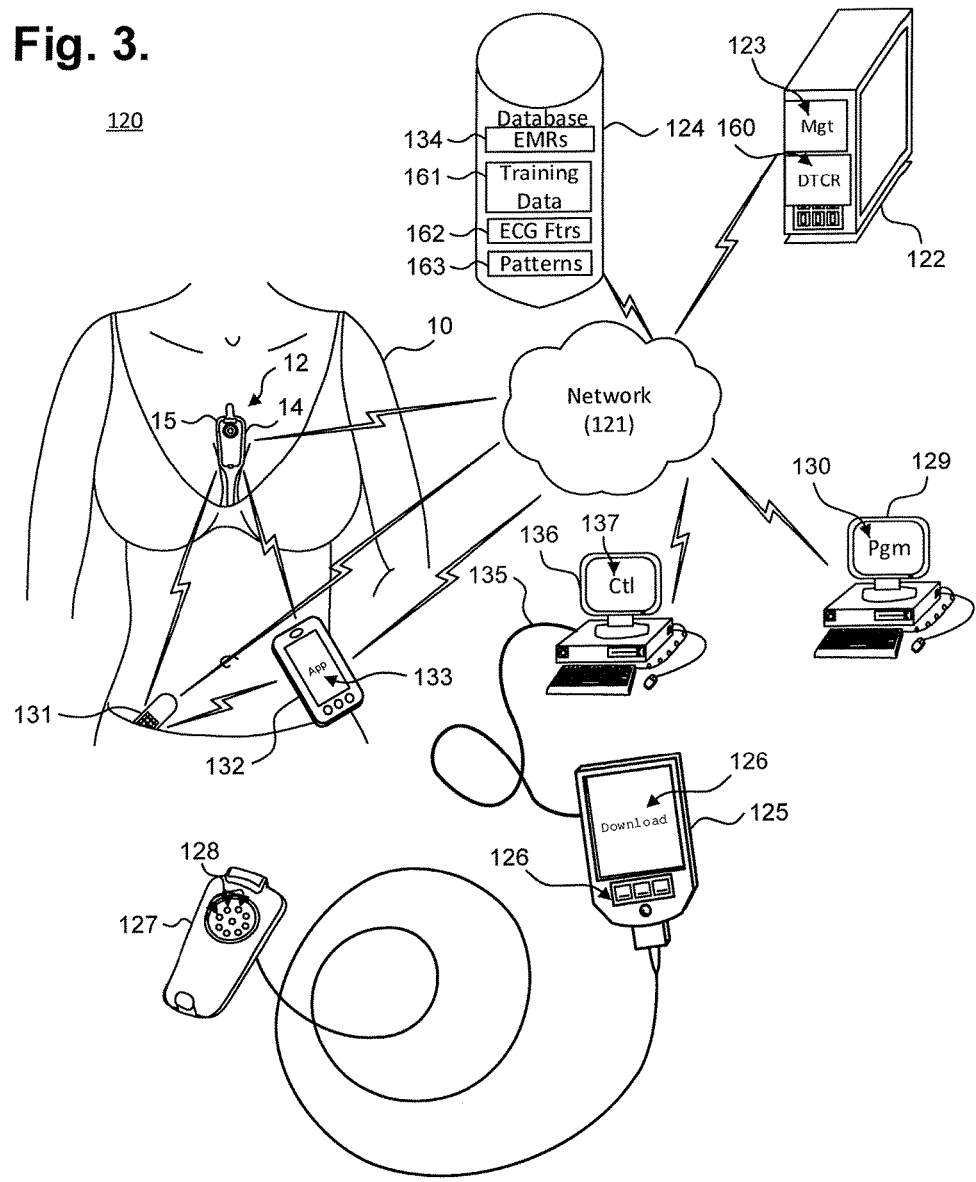
FIG. 3 is a functional block diagram showing a system for remote interfacing of an extended wear electrocardiography and physiological sensor monitor in accordance with one embodiment.

When operated standalone, the monitor recorder 14 of the extended wear electrocardiography and physiological sensor monitor 12 senses and records the patient's ECG data into an onboard memory. In addition, the wearable monitor 12 can interoperate with other devices. FIG. 3 is a functional block diagram showing a system 120 for remote interfacing of an extended wear electrocardiography and physiological sensor monitor 12 in accordance with one embodiment. The monitor recorder 14 is a reusable component that can be fitted during patient monitoring into a non-conductive receptacle provided on the electrode patch 15, as further described infra with reference to FIG. 4, and later removed for offloading of stored ECG data or to receive revised programming. The monitor recorder 14 can then be connected to a download station 125, which could be a programmer or other device that permits the retrieval of stored ECG monitoring data, execution of diagnostics on or programming of the monitor recorder 14, or performance of other functions. The monitor recorder 14 has a set of electrical contacts (not shown) that enable the monitor recorder 14 to physically interface to a set of terminals 128 on a paired receptacle 127 of the download station 125. In turn, the download station 125 executes a communications or offload program 126 ("Offload") or similar program that interacts with the monitor recorder 14 via the physical interface to retrieve the stored ECG monitoring data. The download station 125 could be a server, personal computer, tablet or handheld computer, smart mobile device, or purpose-built programmer designed specific to the task of interfacing with a monitor recorder 14. Still other forms of download station 125 are possible.

Figure 13:
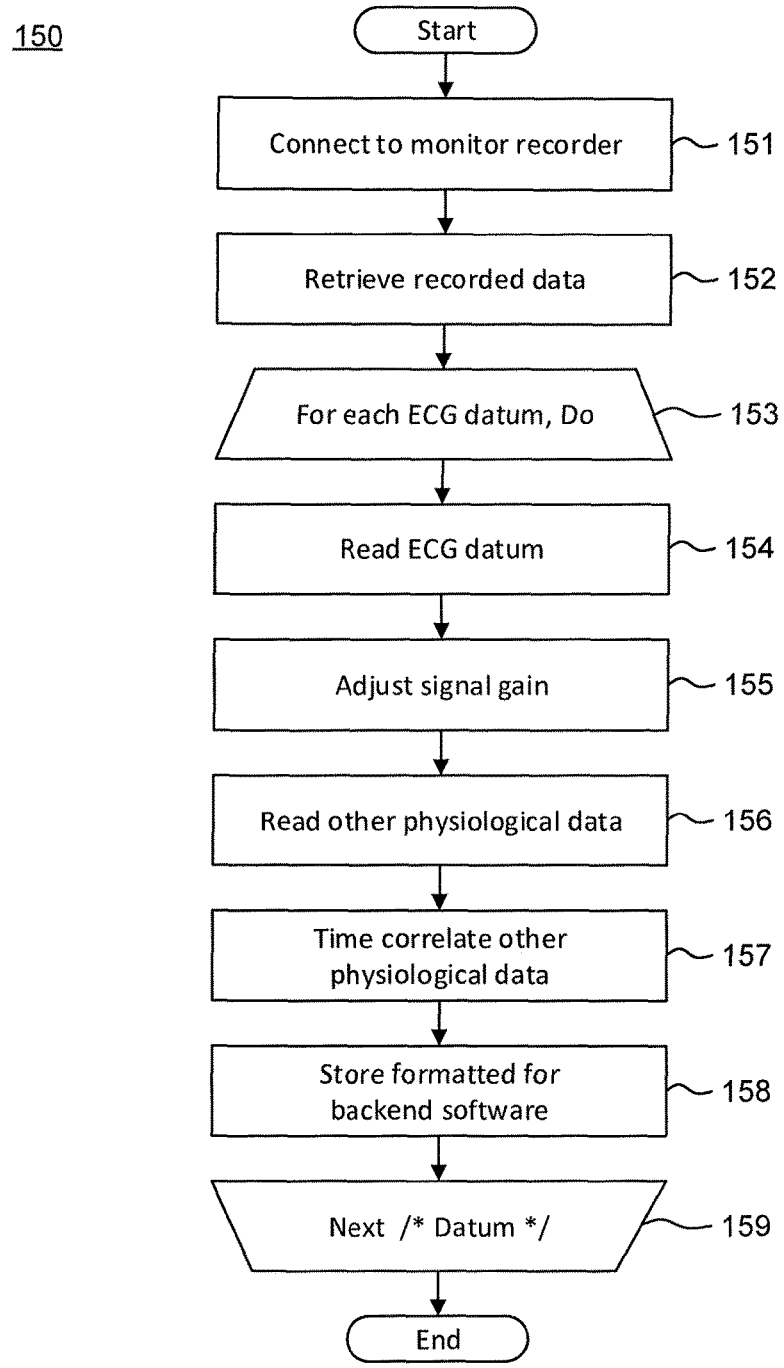
FIG. 13 is a flow diagram showing a method for offloading and converting ECG and other physiological data from an extended wear electrocardiography and physiological sensor monitor in accordance with one embodiment.

Upon retrieving stored ECG monitoring data from a monitor recorder 14, middleware first operates on the retrieved data to adjust the ECG capture quality, as necessary, and to convert the retrieved data into a format suitable for use by third party post-monitoring analysis software, as further described infra with reference to FIG. 13. The formatted data can then be retrieved from the download station 125 over a hard link 135 using a control program 137 ("Ctl") or analogous application executing on a personal computer 136 or other connectable computing device, via a communications link (not shown), whether wired or wireless, or by physical transfer of storage media (not shown). The personal computer 136 or other connectable device may also execute middleware that converts ECG data and other information into a format suitable for use by a third-party post-monitoring analysis program, as further described infra with reference to FIG. 13. Note that formatted data stored on the personal computer 136 would have to be maintained and safeguarded in the same manner as electronic medical records (EMRs) 134 in the secure database 124, as further discussed infra. In a further embodiment, the download station 125 is able to directly interface with other devices over a computer communications network 121, which could be some combination of a local area network and a wide area network, including the Internet, over a wired or wireless connection.

A client-server model could be used to employ a server 122 to remotely interface with the download station 125 over the network 121 and retrieve the formatted data or other information. The server 122 executes a patient management program 123 ("Mgt") or similar application that stores the retrieved formatted data and other information in a secure database 124 cataloged in that patient's EMRs 134. In addition, the patient management program 123 could manage a subscription service that authorizes a monitor recorder 14 to operate for a set period of time or under pre-defined operational parameters.

The patient management program 123, or other trusted application, also maintains and safeguards the secure database 124 to limit access to patient EMRs 134 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 124. The physician would execute an application program 130 ("Pgm"), such as a post-monitoring ECG analysis program, on a personal computer 129 or other connectable computing device, and, through the application 130, coordinate access to his patient's EMRs 134 with the patient management program 123. Other schemes and safeguards to protect and maintain the integrity of patient EMRs 134 are possible. The patient management program 123 can also manage access to the EMRs by a variety of parties that are authorized to access to modify the EMRs, as further described in " . . . ," which is hereby incorporated by reference.

Prior to Storing the Results of the Monitoring into the EMRs, the EMRs

The wearable monitor 12 can interoperate wirelessly with other wearable physiology monitors and activity sensors 131, such as activity trackers worn on the wrist or body, and with mobile devices 133, including smart watches and smartphones. Wearable physiology monitors and activity sensors 131 encompass a wide range of wirelessly interconnectable devices that measure or monitor a patient's physiological data, such as heart rate, temperature, blood pressure, respiratory rate, blood pressure, blood sugar (with appropriate subcutaneous probe), oxygen saturation, minute ventilation, and so on; physical states, such as movement, sleep, footsteps, and the like; and performance, including calories burned or estimated blood glucose level. The physiology sensors in non-wearable mobile devices, particularly smartphones, are generally not meant for continuous tracking and do not provide medically precise and actionable data sufficient for a physician to prescribe a surgical or serious drug intervention; such data can be considered screening information that something may be wrong, but not data that provides the highly precise information that may allow for a surgery, such as implantation of a pacemaker for heart block or a defibrillator for ventricular tachycardia, or the application of serious medications, like blood thinners for atrial fibrillation or a cardiac ablation procedure. Such devices, like smartphones, are better suited to pre- and post-exercise monitoring or as devices that can provide a signal that something is wrong, but not in the sufficient detail and validation to allow for medical action. Conversely, medically actionable wearable sensors and devices sometimes provide continuous recording for relatively short time periods, but must be paired with a smartphone or computer to offload and evaluate the recorded data, especially if the data is of urgent concern.

Wearable physiology monitors and activity sensors 131, also known as "activity monitors," and to a lesser extent, "fitness" sensor-equipped mobile devices 133, can trace their life-tracking origins to ambulatory devices used within the medical community to sense and record traditional medical physiology that could be useful to a physician in arriving at a patient diagnosis or clinical trajectory, as well as from outside the medical community, from, for instance, sports or lifestyle product companies who seek to educate and assist individuals with self-quantifying interests. Data is typically tracked by the wearable physiology monitors or activity sensors 131 and mobile device 133 for only the personal use of the wearer. The physiological monitoring is strictly informational, even where a device originated within the medical community, and the data is generally not time-correlated to physician-supervised monitoring. Importantly, medically-significant events, such as cardiac rhythm disorders, including tachyarrhythmias, like ventricular tachycardia or atrial fibrillation, and bradyarrhythmias, like heart block, while potentially detectable with the appropriate diagnostic heuristics, are neither identified nor acted upon by the wearable physiology monitors and activity sensors 131 and the mobile device 133.

Frequently, wearable physiology monitors and activity sensors 131 are capable of wirelessly interfacing with mobile devices 133, particularly smart mobile devices, including so-called "smartphones" and "smart watches," as well as with personal computers and tablet or handheld computers, to download monitoring data either in real-time or in batches. The wireless interfacing of such activity monitors is generally achieved using transceivers that provide low-power, short-range wireless communications, such as Bluetooth, although some wearable physiology monitors and activity sensors 131, like their mobile device cohorts, have transceivers that provide true wireless communications services, including 4G or better mobile telecommunications, over a telecommunications network. Other types of wireless and wired interfacing are possible.

Where the wearable physiology monitors and activity sensors 131 are paired with a mobile device 133, the mobile device 133 executes an application ("App") that can retrieve the data collected by the wearable physiology monitor and activity sensor 131 and evaluate the data to generate information of interest to the wearer, such as an estimation of the effectiveness of the wearer's exercise efforts. Where the wearable physiology monitors and activity sensors 131 has sufficient onboard computational resources, the activity monitor itself executes an app without the need to relay data to a mobile device 133. Generally, such more computationally-capable wearable physiology monitors and activity sensors are also equipped with wireless communications services transceivers, such as found in some smart watches that combine the features of activity monitors with mobile devices. Still other activity monitor and mobile device functions on the collected data are possible.

In a further embodiment, a wearable physiology monitor, activity sensor 131, or mobile device 133 worn or held by the patient 10, or otherwise be used proximal to the patient's body, can be used to first obtain and then work collaboratively with a more definitive monitor recorder 14 to enable the collection of physiology by the monitor recorder 14 before, during, and after potentially medically-significant events. The wearable physiology monitor, activity sensor 131, or mobile device 133 must be capable of sensing cardiac activity, particularly heart rate or rhythm, or other types of physiology or measures, either directly or upon review of relayed data. Where the wearable physiology monitor or activity sensor 131 is paired with a mobile device 133, the mobile device 133 serves as a relay device and executes an application that will trigger the dispatch of a monitor recorder 14 to the patient 10 upon detecting potentially medically-significant events in the data provided by the paired activity monitor, such as cardiac rhythm disorders, including tachyarrhythmias and bradyarrhythmias. If the mobile device 133 is itself performing the monitoring of the patient's physiology, the mobile device 133 executes an application that will trigger the dispatch of a monitor recorder 14 to the patient 10 in near-real time upon detecting potentially medically-significant events, thereby avoiding the delay incurred by data relay from an activity monitor.

Finally, if the wearable physiology monitor or activity sensor 131 has sufficient onboard computational resources and also is equipped with a wireless communications services transceiver, the wearable physiology monitor or activity sensor 131 effectively becomes the mobile device 133 and executes an application that will trigger the dispatch of a monitor recorder 14 to the patient 10 in near-real time upon detecting potentially medically-significant events without the need to first interface with a mobile device 133. Still other configurations of the detection app are possible.

The act of triggering the dispatch of a monitor recorder 14 represents the first step in a cascade of possible medical interventions of potentially increasing seriousness and urgency. Sensors 131 and devices 133 are generally not capable of detecting and recording medically precise and actionable data, whereas, as a device designed for extended wear, the monitor recorder 14 continually monitors the patient's physiology over a long time period and will capture any medically-actionable data leading up to, throughout the occurrence of, and following an event of potential medical concern.

The monitoring data recorded by the monitor recorder 14 can be uploaded directly into the patient's EMRs 134, either by using a mobile device 133 as a conduit for communications with a server 122 coupled to a secure database 124 within which the patient's EMRs 134 are stored, or directly to the server 122, if the monitor recorder 14 is appropriately equipped with a wireless transceiver or similar external data communications interface, as further described infra. Thus, the data recorded by the monitor recorder 14 would directly feed into the patient's EMRs 134, thereby allowing the data to be made certifiable for immediate use by a physician or healthcare provider. No intermediate steps would be necessary when going from cutaneously sensing cardiac electric signals and collecting the patient's physiology using a monitor recorder 14 to presenting that recorded data to a physician or healthcare provider for medical diagnosis and care. The direct feeding of data from the monitor recorder 14 to the EMRs 134 clearly establishes the relationship of the data, as recorded by the monitor recorder 14, to the patient 10 that the physician is seeing and appropriately identifies any potentially medically-significant event recorded in the data as originating in the patient 10 and nobody else. Based on the monitoring data, physicians and healthcare providers can rely on the data as certifiable and can directly proceed with determining the appropriate course of treatment for the patient 10, including undertaking further medical interventions as appropriate. In a further embodiment, the server 122 can evaluate the recorded data, as fed into the patient's EMRs 134, to refer the patient 10 for medical care to a general practice physician or medical specialist, for instance, a cardiac electrophysiologist referral from a cardiologist when the recorded data indicates an event of sufficient potential severity to warrant the possible implantation of a pacemaker for heart block or a defibrillator for ventricular tachycardia. Other uses of the data recorded by the monitor recorder 14 are possible.

For instance, a patient 10 who has previously suffered heart failure is particularly susceptible to ventricular tachycardia following a period of exercise or strenuous physical activity. A wearable sensor 131 or device 133 that includes a heart rate monitor would be able to timely detect an irregularity in heart rhythm. The application executed by the sensor 131 or device 133 allows those devices to take action by triggering the dispatch of a monitor recorder 14 to the patient 10, even though the data recorded by the sensor 131 or device 133 is itself generally medically-insufficient for purposes of diagnosis and care. Thus, rather than passively recording patient data, the sensor 131 or device 133 takes on an active role in initiating the provisioning of medical care to the patient 10 and starts a cascade of appropriate medical interventions under the tutelage of and followed by physicians and trained healthcare professionals.

In a still further embodiment, the monitor recorder 14 could upload an event detection application to the sensor 131 or device 133 to enable those devices to detect those types of potentially medically-significant events, which would trigger the dispatch of a monitor recorder 14 to the patient 10. Alternatively, the event detection application could be downloaded to the sensor 131 or device 133 from an online application store or similar online application repository. Finally, the monitor recorder 14 could use the sensor 131 or device 133 to generate an appropriate alert, including contacting the patient's physician or healthcare services, via wireless (or wired) communications, upon detecting a potentially medically-significant event or in response to a patient prompting.

The patient 10 could be notified by the sensor 131 or device 133, through the sensor's or device's user interface, that an event of potential medical concern has been detected coupled with an offer to have a monitor recorder 14 sent out to the patient 10, assuming that the patient 10 is not already wearing a monitor recorder 14. Alternatively, the sensor 131 or device 133 could unilaterally send out a request for a monitor recorder 14. The request for a monitor recorder 14 could be sent via wireless (or wired) communications to the patient's physician, a medical service provider organization, a pharmacy, an emergency medical service, or other appropriate healthcare entity that would, in turn, physically provide the patient with a monitor recorder 14. The patient 10 could also be told to pick up a monitor recorder 14 directly from one of the above-identified sources.

Conventional Holter monitors, as well as the ZIO XT Patch and ZIO Event Card devices, described supra, are currently available only by a physician's prescription for a specific patient 10. As a result, the physiological data recorded by these monitors and devices are assumed by healthcare professional to belong to the patient 10. In this prescriptive medicine context, grave questions as to the authenticity of the patient's identity and the data recorded do not generally arise, although current medical practice still favors requesting affirmative patient and caregiver identification at every step of healthcare provisioning. As a device intended for adoption and usage broader than prescriptive medicine, the monitor recorder 14 carries the potential to be used by more than one individual, which can raise concerns as to the veracity of the data recorded.

In a still further embodiment, the mobile device 133, or, if properly equipped, the activity monitor, can be used to help authenticate the patient 10 at the outset of and throughout the monitoring period. The mobile device 133 (or activity monitor) must be appropriately equipped with a digital camera or other feature capable of recording physical indicia located within the proximity of the mobile device 133. For instance, the Samsung Galaxy S5 smartphone has both a biometric fingerprint reader and autofocusing digital camera built in. Upon receipt of a monitor recorder 14, the patient 10 can use the photographic or other recording features of the mobile device 133 (or activity monitor) to physically record the placement and use of the monitor recorder 14. For instance, the patient 10 could take a picture or make a video of the monitor recorder 14 using as applied to the chest using the built-in digital camera. The patient 10 could also swipe a finger over the biometric fingerprint reader. Preferably, the patient 10 would include both his or her face or similar uniquely-identifying marks or indicia, such as a scar, tattoo, body piercing, or RFID chip, plus any visible or electronic indicia on the outside of the monitor recorder's housing, as further described infra with reference to FIG. 5, in the physical recording. The physical recording would then be sent by the mobile device 133 (or activity monitor) via wireless (or wired) communications to the patient's physician's office or other appropriate caregiver, thereby facilitating the authentication of the data recorded by the monitor recorder 14. Alternatively, the physical recording could be securely stored by the monitor recorder 14 as part of the monitoring data set.

The mobile device 133 could also serve as a conduit for providing the data collected by the wearable physiology monitor or activity sensor 131 to at least one server 122, or, similarly, the wearable physiology monitor or activity sensor 131 could itself directly provide the collected data to the server 122. The server 122 could then merge the collected data into the wearer's EMRs 134 in the secure database 124, if appropriate (and permissible), or the server 122 could perform an analysis of the collected data, perhaps based by comparison to a population of like wearers of the wearable physiology monitor or activity sensor 131. Still other server 122 functions on the collected data are possible.

Figure 9:
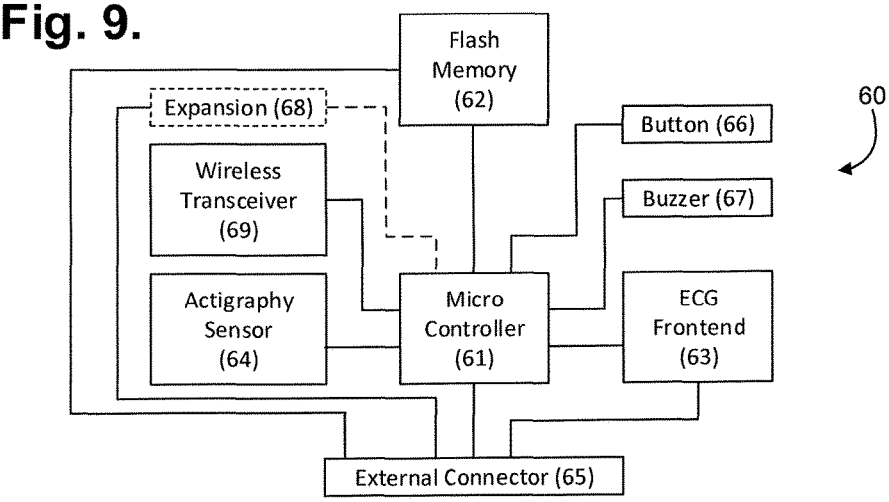
FIG. 9 is a functional block diagram showing the component architecture of the circuitry of the monitor recorder of FIG. 4.
Figure 10:
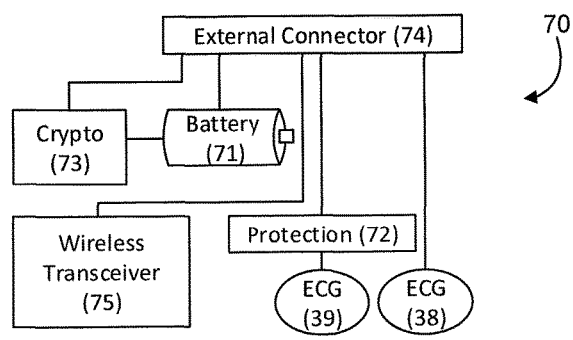
FIG. 10 is a functional block diagram showing the circuitry of the extended wear electrode patch of FIG. 4.

Finally, the monitor recorder 14 can also be equipped with a wireless transceiver, as further described infra with reference to FIGS. 9 and 10. Thus, when wireless-enabled, both wearable physiology monitors, activity sensors 131, and mobile devices 133 can wirelessly interface with the monitor recorder 14, which could either provide data or other information to, or receive data or other information from an interfacing device for relay to a further device, such as the server 122, analysis, or other purpose. In addition, the monitor recorder 14 could wirelessly interface directly with the server 122, personal computer 129, or other computing device connectable over the network 121, when the monitor recorder 14 is appropriately equipped for interfacing with such devices. Still other types of remote interfacing of the monitor recorder 14 are possible.

In addition to storing the data received from the monitor 14 recorder as part of the patient's EMR 134, the server 122 can perform other analyses that can speed up the processing of the results of the monitoring. For example, the server 122 executes an adaptive atrial fibrillation detector 160, which divides ECG data collected using the monitor 12 into segments and analyzes each segment to determine whether the patient was experiencing atrial fibrillation at the time the segment was recorded. The adaptive atrial fibrillation detector 160 can be implemented by a convolutional neural network utilizing, for example, a one dimensional formulation for use with ECG data. Additionally, the adaptive atrial fibrillation detector 160 can include hidden layers for performing the classification. In the example described below, two convolutional or pooling hidden layers, and two fully-connected hidden layers are utilized. However, other number of layers are possible.

Prior to being used for classification of the segments, the adaptive atrial fibrillation detector 160 is trained on training data 161, which can be stored in the database 124. The training data 161 includes data files from ambulatory ECG monitors associated with a group of patients. The patients can be selected randomly or identified based on patient condition. In one embodiment, between 200 and 250 files can be collected from different ECG ambulatory monitors, such as monitors 12, though other kinds of monitors are possible, and used as training data. The ambulatory monitors used to collect the ECG data can include the monitor described above with respect to FIGS. 1-10, as well as other types of monitors. The data file collected from each ECG ambulatory monitor can each include up to or more than 64 MB of data, though other sizes are also possible. As further described below, with reference to FIG. 15, the detector 160 divides the training data 161 into segments of a recorded ECG signal recorded during a particular ECG window. In one embodiment, the duration of each temporal period can be between 2 and 60 seconds, such as 20 seconds, though other durations are also possible.

The database 124 further holds a plurality of ECG features 162, with each feature being one or more elements of an ECG trace, such as particular wave (such as P, Q, R, S, or T waves) or a combination of waves (such as the QRS complex). Waves or combinations of waves of different shapes can be stored as different features 161. For example, a narrow QRS complex and a wide QRS complex can be stored as different features. Similarly, P waves of different height can be stored as different features 162. The features 162 can be extracted from the ECG traces from the training data 161, though other sources are also possible. In one embodiment, a total of 32 features 162 are stored in the database 124, though other numbers of features 162 are possible.

The server 122 receives annotations 163 of patterns of ECG features 162 identified within the training data 161 and provides the annotated patterns 163 to the detector 161. Each annotation states whether a particular pattern of features is associated with atrial fibrillation. For example, a pattern of features can include irregular intervals between two or more successive R waves can be annotated to be associated with atrial fibrillation, though other kinds of patterns are also possible. Not all irregular patterns are necessarily atrial fibrillation. Many other disorders can mimic atrial fibrillation on the basis of just irregular rhythms, such as frequent premature atrial or ventricular contractions or atrial flutter and atrial tachycardia with variable AV conduction. Thus, the P-wave sensitive nature of the Carnation Ambulatory Monitor™ facilitates the machine learning specificity and sensitivity of true atrial fibrillation detection. The annotations 163 are made by a user, such as a physician, or using another classification tool. The annotated patterns 163 of features 162 are run through the detector 160 one or more times, training the detector 160 to recognize patterns of features associated with atrial fibrillation.

While the annotated patterns 163, the ECG features 162, and the training data 161 are shown with reference to FIG. 3 as being stored in the same database 124 as the EMRs 134, in a further embodiment, the annotated patterns 163, the ECG features 162, and the training data 161 could be stored in a different database that is interfaced to the at least one server 122 either directly or through the network 121.

The trained classifier is subsequently used to analyze additional ECG data segments and classify the data as either associated with atrial fibrillation or not, as further described below with reference to FIG. 16. Upon classifying an ECG segment as associated with atrial fibrillation, the server 122 can store the classified ECG segments as part of the EMRs 134 stored in the database 124, as well as take other actions, such as provide an alert, such as via e-mail or text message, to appropriate medical personnel that could lead to further evaluation of the classified data and the patient receiving an appropriate medical treatment. Other kinds of reports that the server 122 can make are possible. Other kinds of actions that the server 122 can take are possible.

Figure 4:
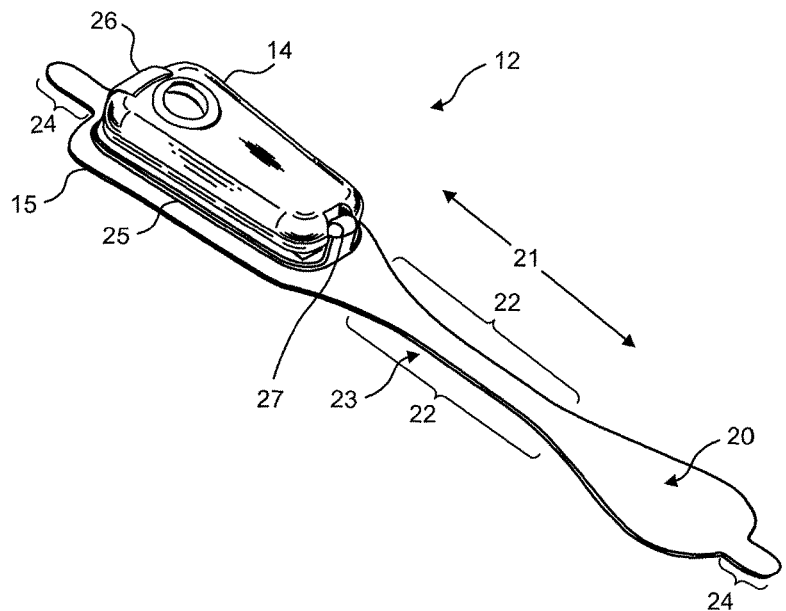
FIG. 4 is a perspective view showing an extended wear electrode patch with a monitor recorder inserted.

During use, the electrode patch 15 is first adhered to the skin along the sternal midline 16 (or immediately to either side of the sternum 13). A monitor recorder 14 is then snapped into place on the electrode patch 15 to initiate ECG monitoring. FIG. 4 is a perspective view showing an extended wear electrode patch 15 with a monitor recorder 14 in accordance with one embodiment inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Pat. No. 9,545,204, issued Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Pat. No. 9,730,593, issued Aug. 15, 2017, the disclosure which is incorporated by reference. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
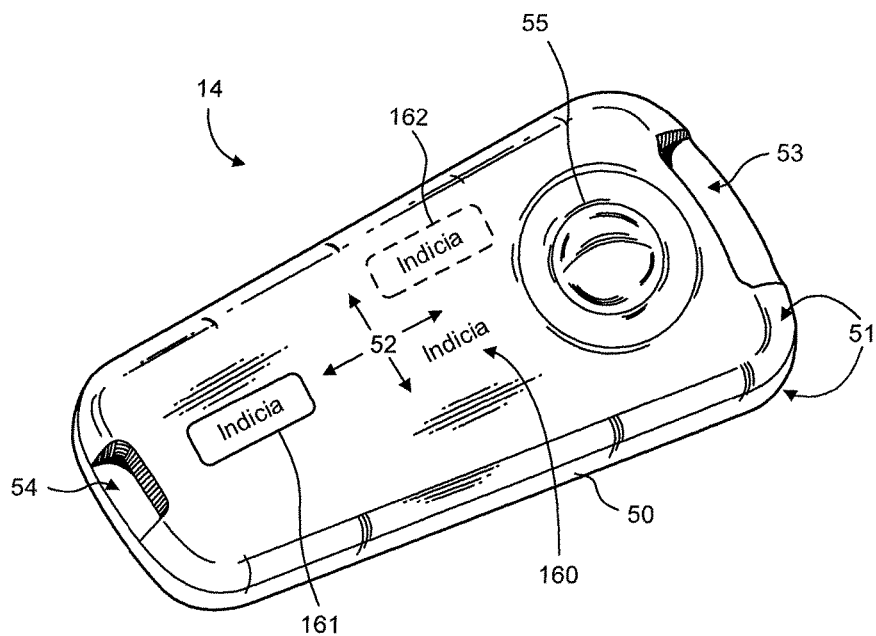
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Pat. No. D717,955, issued Nov. 18, 2014, the disclosure of which is incorporated by reference. In addition, a label, barcode, QR code, or other visible or electronic indicia is printed on the outside of, applied to the outside of, or integrated into the sealed housing 50 to uniquely identify the monitor recorder 14 and can include a serial number, manufacturing lot number, date of manufacture, and so forth. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
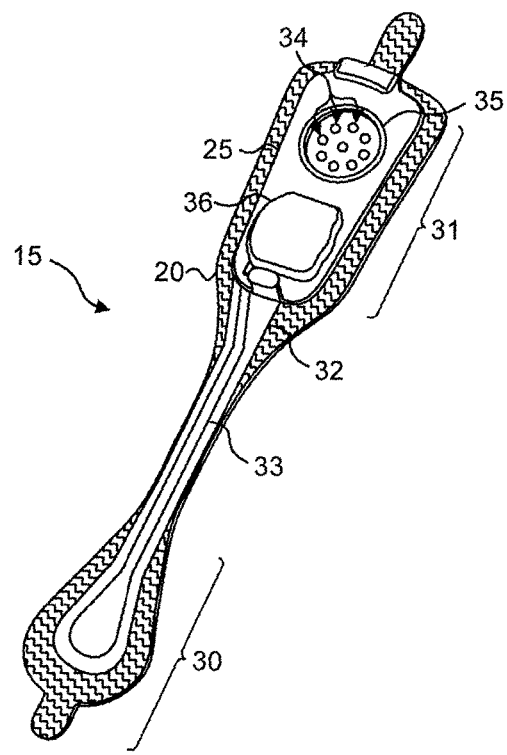
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 7:
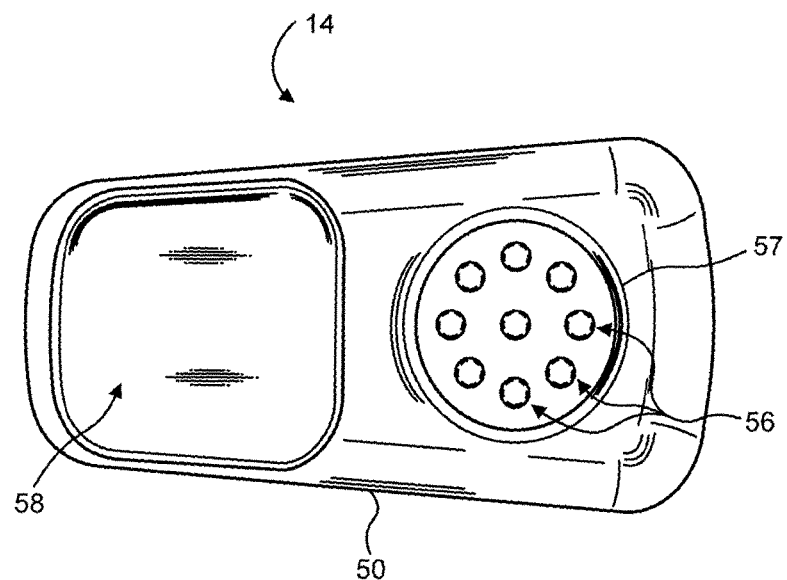
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 8:
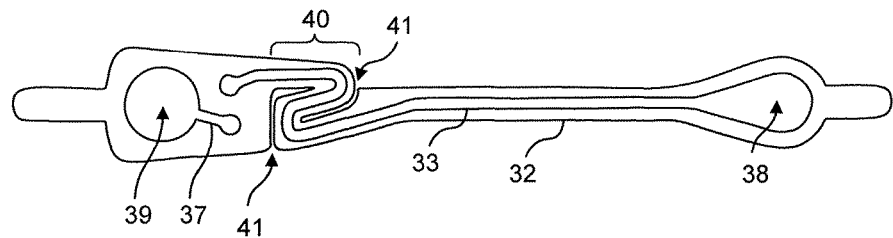
FIG. 8 is a top view showing the flexible circuit of the extended wear electrode patch of FIG. 4 when mounted above the flexible backing.

Unlike the flexible backing 20, the flexible circuit 32 is only able to bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

ECG monitoring and other functions performed by the monitor recorder 14 are provided through a micro controlled architecture. FIG. 9 is a functional block diagram showing the component architecture of the circuitry 60 of the monitor recorder 14 of FIG. 4. The circuitry 60 is externally powered through a battery provided in the non-conductive receptacle 25 (shown in FIG. 6). Both power and raw ECG signals, which originate in the pair of ECG electrodes 38, 39 (shown in FIG. 8) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions.

Operation of the circuitry 60 of the monitor recorder 14 is managed by a microcontroller 61. The micro-controller 61 includes a program memory unit containing internal flash memory that is readable and writeable. The internal flash memory can also be programmed externally. The microcontroller 61 draws power externally from the battery provided on the electrode patch 15 via a pair of the electrical contacts 56. The microcontroller 61 connects to the ECG front end circuit 63 that measures raw cutaneous electrical signals and generates an analog ECG signal representative of the electrical activity of the patient's heart over time.

The circuitry 60 of the monitor recorder 14 also includes a flash memory 62, which the micro-controller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses, such as described in commonly-assigned U.S. Pat. No. 9,737,224, issued Aug. 22, 2017, the disclosure of which is incorporated by reference.

The circuitry 60 of the monitor recorder 14 includes a wireless transceiver 69 that can provides wireless interfacing capabilities. The wireless transceiver 69 also draws power externally from the battery provided on the electrode patch 15 via a pair of the electrical contacts 56. The wireless transceiver 69 can be implemented using one or more forms of wireless communications, including the IEEE 802.11 computer communications standard, that is Wi-Fi; the 4G mobile phone mobile standard; the Bluetooth data exchange standard; or other wireless communications or data exchange standards and protocols. The type of wireless interfacing capability could limit the range of interoperability of the monitor recorder 14; for instance, Bluetooth-based implementations are designed for low power consumption with a short communications range.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the micro-controller 61 provided over one of the electrical contacts 56. The physiology sensor can include an $SpO_2$ sensor, blood pressure sensor, temperature sensor, respiratory rate sensor, glucose sensor, airflow sensor, volumetric pressure sensing, or other types of sensor or telemetric input sources. For instance, the integration of an airflow sensor is described in commonly-assigned U.S. Pat. No. 9,364,155, issued Jun. 14, 2016, the disclosure which is incorporated by reference.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

While the monitor recorder 14 operates under micro control, most of the electrical components of the electrode patch 15 operate passively. FIG. 10 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14, such as described in commonly-assigned U.S. Pat. No. 9,655,538, issued May 23, 2017, the disclosure which is incorporated by reference.

In a further embodiment, the circuitry 70 of the electrode patch 15 includes a wireless transceiver 75, in lieu the including of the wireless transceiver 69 in the circuitry 60 of the monitor recorder 14, which interfaces with the microcontroller 61 over the microcontroller's expansion port via the external connector 74.

Figure 11:
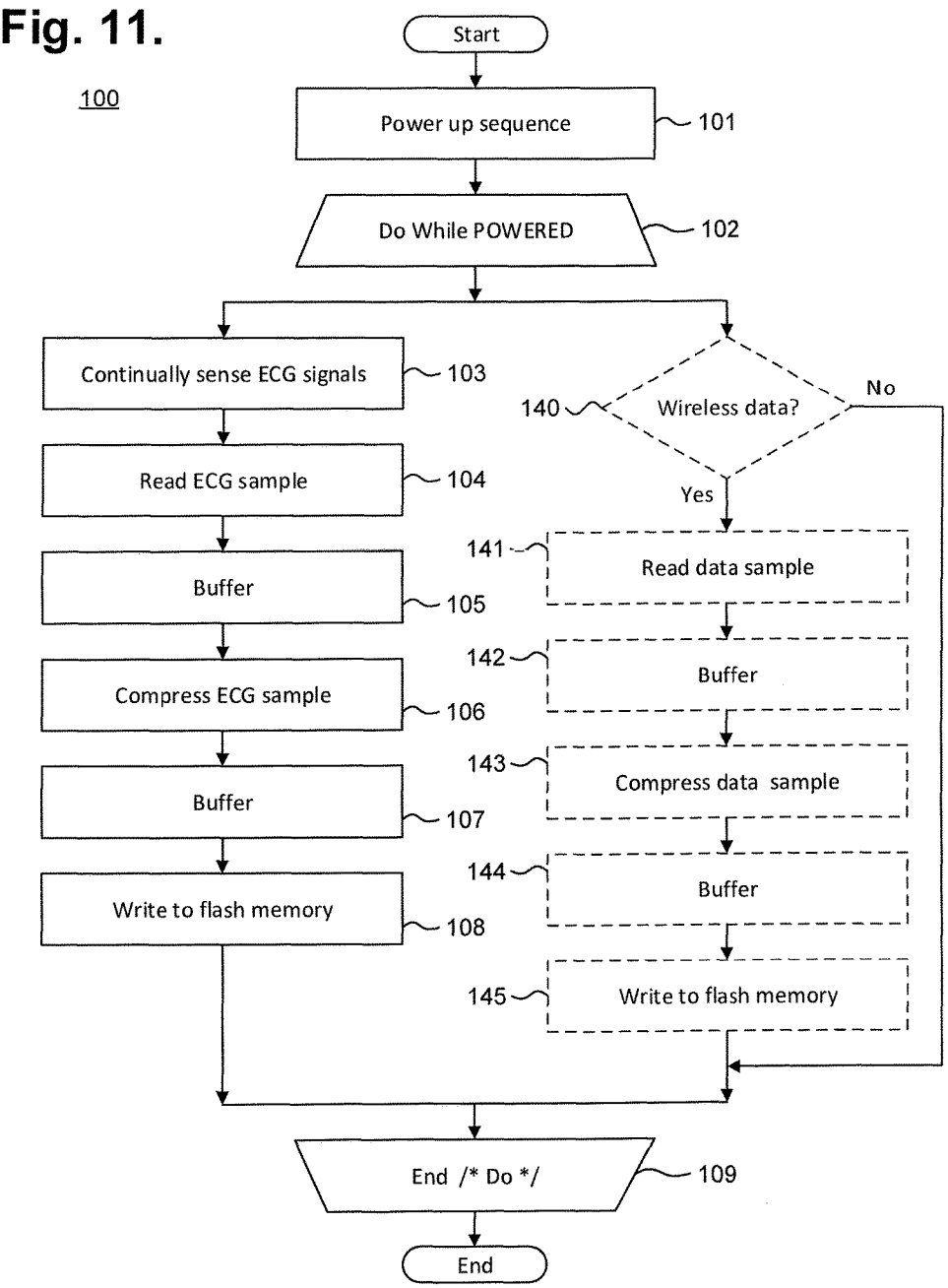
FIG. 11 is a flow diagram showing a monitor recorder-implemented method for monitoring ECG data for use in the monitor recorder of FIG. 4.

The monitor recorder 14 continuously monitors the patient's heart rate and physiology. FIG. 11 is a flow diagram showing a monitor recorder-implemented method 100 for monitoring ECG data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 12:
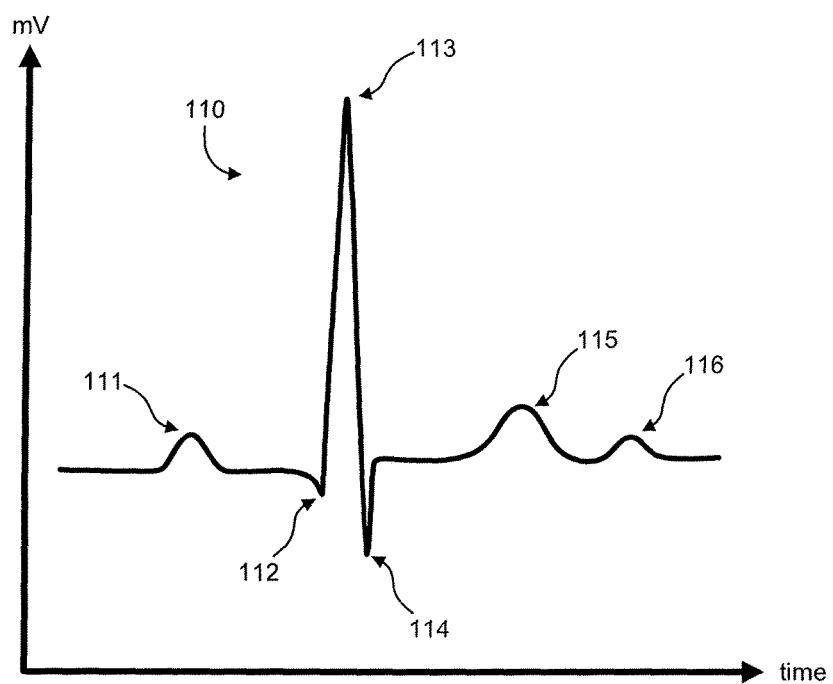
FIG. 12 is a graph showing, by way of example, a typical ECG waveform.

Following satisfactory completion of the power up sequence, an iterative processing loop (steps 102-109) is continually executed by the microcontroller 61. During each iteration (step 102) of the processing loop, the ECG frontend 63 (shown in FIG. 9) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal output front end 63. FIG. 12 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q wave 112, followed by a larger upward deflection of an R-wave 113, and terminated with a downward waveform of the S wave 114, collectively representative of ventricular depolarization. The T wave 115 is normally a modest upward waveform, representative of ventricular depolarization, while the U wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Each sampled ECG signal, in quantized and digitized form, is temporarily staged in buffer (step 105), pending compression preparatory to storage in the flash memory 62 (step 106). Following compression, the compressed ECG digitized sample is again buffered (step 107), then written to the flash memory 62 (step 108) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

In a further embodiment, the monitor recorder 14 also continuously receives data from wearable physiology monitors or activity sensors 131 and mobile devices 133 (shown in FIG. 3). The data is received in a conceptually-separate execution thread as part of the iterative processing loop (steps 102-109) continually executed by the microcontroller 61. During each iteration (step 102) of the processing loop, if wireless data is available (step 140), a sample of the wireless is read (step 141) by the microcontroller 61 and, if necessary, converted into a digital signal by the onboard ADC of the microcontroller 61. Each wireless data sample, in quantized and digitized form, is temporarily staged in buffer (step 142), pending compression preparatory to storage in the flash memory 62 (step 143). Following compression, the compressed wireless data sample is again buffered (step 144), then written to the flash memory 62 (step 145) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

The monitor recorder 14 stores ECG data and other information in the flash memory 62 (shown in FIG. 9) using a proprietary format that includes data compression. As a result, data retrieved from a monitor recorder 14 must first be converted into a format suitable for use by third party post-monitoring analysis software. FIG. 13 is a flow diagram showing a method 150 for offloading and converting ECG and other physiological data from an extended wear electrocardiography and physiological sensor monitor 12 in accordance with one embodiment. The method 150 can be implemented in software and execution of the software can be performed on a download station 125, which could be a programmer or other device, or a computer system, including a server 122 or personal computer 129, such as further described supra with reference to FIG. 3, as a series of process or method modules or steps. For convenience, the method 150 will be described in the context of being performed by a personal computer 136 or other connectable computing device (shown in FIG. 3) as middleware that converts ECG data and other information into a format suitable for use by a third-party post-monitoring analysis program. Execution of the method 150 by a computer system would be analogous mutatis mutandis.

Initially, the download station 125 is connected to the monitor recorder 14 (step 151), such as by physically interfacing to a set of terminals 128 on a paired receptacle 127 or by wireless connection, if available. The data stored on the monitor recorder 14, including ECG and physiological monitoring data, other recorded data, and other information are retrieved (step 152) over a hard link 135 using a control program 137 ("Ctl") or analogous application executing on a personal computer 136 or other connectable computing device.

The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 153-159) in an iterative processing loop. During each iteration (step 153), the ECG datum is read (step 154) and, if necessary, the gain of the ECG signal is adjusted (step 155) to compensate, for instance, for relocation or replacement of the electrode patch 15 during the monitoring period.

In addition, depending upon the configuration of the wearable monitor 12, other physiological data (or other information), including patient events, such as a fall, peak activity level, sleep detection, Detection of patient activity levels and states, and so on, may be recorded along with the ECG monitoring data. For instance, actigraphy data may have been sampled by the actigraphy sensor 64 based on a sensed event occurrence, such as a sudden change in orientation due to the patient taking a fall. In response, the monitor recorder 14 will embed the actigraphy data samples into the stream of data, including ECG monitoring data, that is recorded to the flash memory 62 by the micro-controller 61. Post-monitoring, the actigraphy data is temporally matched to the ECG data to provide the proper physiological context to the sensed event occurrence. As a result, the three-axis actigraphy signal is turned into an actionable event occurrence that is provided, through conversion by the middleware, to third party post-monitoring analysis programs, along with the ECG recordings contemporaneous to the event occurrence. Other types of processing of the other physiological data (or other information) are possible.

Thus, during execution of the middleware, any other physiological data (or other information) that has been embedded into the recorded ECG monitoring data is read (step 156) and time-correlated to the time frame of the ECG signals that occurred at the time that the other physiological data (or other information) was noted (step 157). Finally, the ECG datum, signal gain adjusted, if appropriate, and other physiological data, if applicable and as time-correlated, are stored in a format suitable to the backend software (step 158) used in post-monitoring analysis.

In a further embodiment, the other physiological data, if apropos, is embedded within an unused ECG track. For example, the SCP-ENG standard allows multiple ECG channels to be recorded into a single ECG record. The monitor recorder 14, though, only senses one ECG channel. The other physiological data can be stored into an additional ECG channel, which would otherwise be zero-padded or altogether omitted. The backend software would then be able to read the other physiological data in context with the single channel of ECG monitoring data recorded by the monitor recorder 14, provided the backend software implemented changes necessary to interpret the other physiological data. Still other forms of embedding of the other physiological data with formatted ECG monitoring data, or of providing the other physiological data in a separate manner, are possible.

Processing continues (step 159) for each remaining ECG datum, after which the processing loop is exited and execution terminates. Still other operations and steps are possible.

Figure 14:
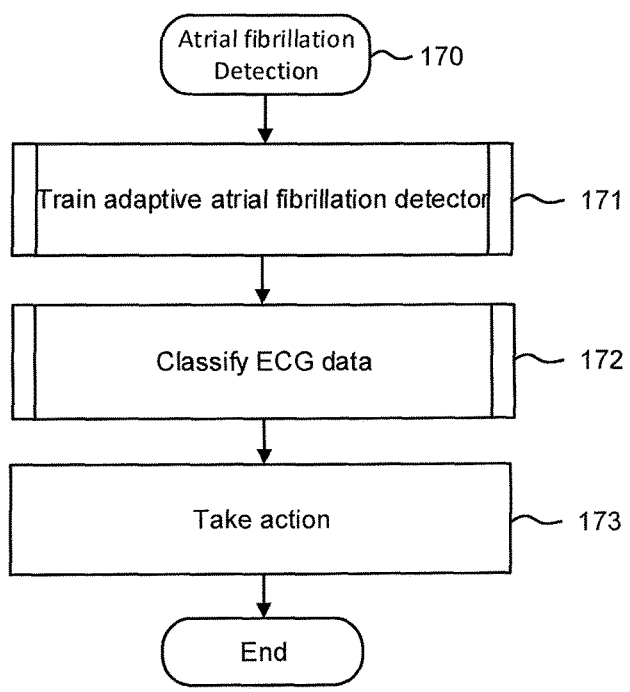
FIG. 14 is a flow diagram showing a method machine-learning-based atrial fibrillation detection with the aid of a digital computer in accordance with one embodiment.

Using machine-learning to detect atrial fibrillation using patterns of ECG features that are known to be indicative of atrial fibrillation allows more flexibility in detecting instances of atrial fibrillation than when the detection is based on a single set of predefined parameters. FIG. 14 is a flow diagram showing a method 170 machine-learning-based atrial fibrillation detection with the aid of a digital computer in accordance with one embodiment. The method can be implemented on the server 122 of FIG. 3, though other implementations are also possible. Prior to classification of ECG data as being indicative of atrial fibrillation, an adaptive atrial fibrillation detector is trained, as further described with reference to FIG. 15 below (step 171). In one example, the adaptive atrial fibrillation detector can be implemented by a convolutional neural network that represents a processing device, such as an algorithm executed by a computer processor or actual hardware. Other types of network systems are possible.

ECG data collected from a patient via a ECG monitor, such as the monitor described above with respect to FIGS. 1-10, though other monitors are possible, is analyzed to determine presence of portions of the data indicative of atrial fibrillation, as further described below with reference to FIG. 16 (172). An action is taken following the analysis (step 173), ending the method 170. Such action can include sending a report of the analysis, such as via mail, though other ways of providing the report are possible, to the patient, the physician who prescribed the monitoring, or another party authorized to receive the report. If the analysis reveals portions of ECG data being associated with atrial fibrillation, an alert can also be sent electronically, such as via an e-mail or an SMS message, to the patient, the physician's patient, or another party authorized to receive the alert.

Further, a detected pattern can be added to the ECG training data and subsequently used to train the adaptive atrial fibrillation detector. Other actions are also possible.

Figure 15:
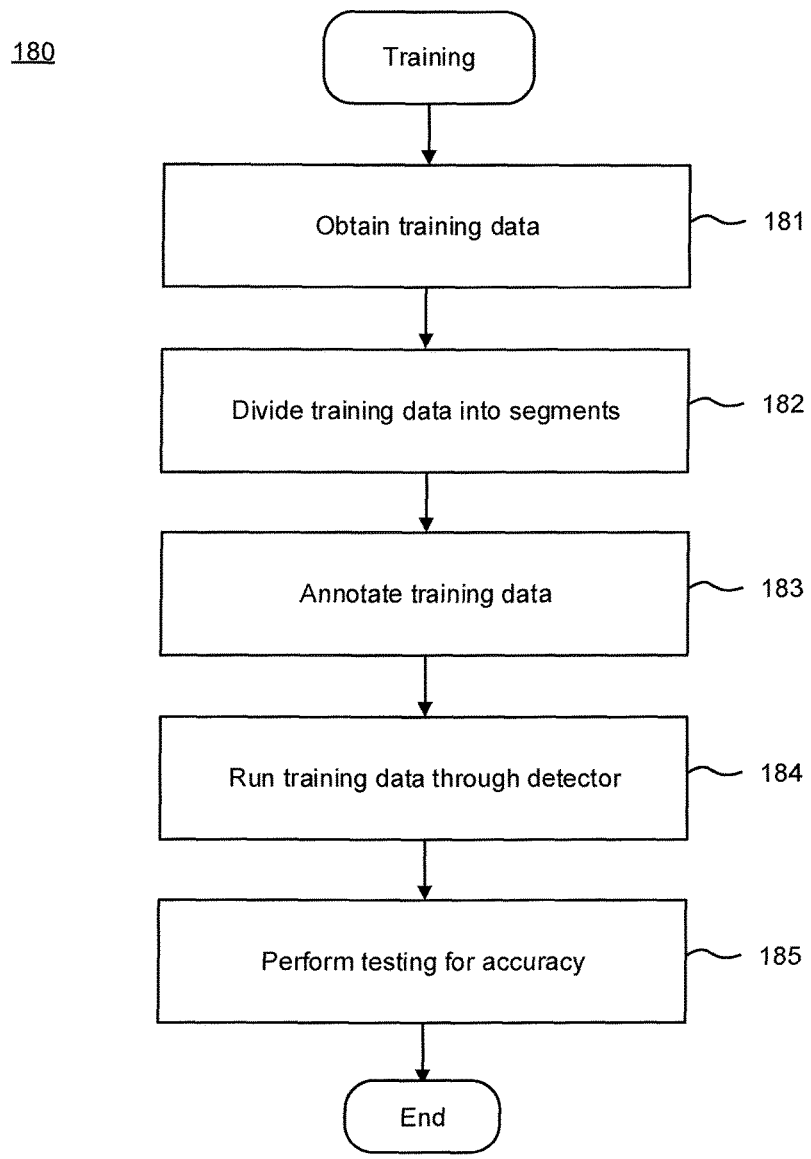
FIG. 15 is a flow diagram showing, by way of example, a routine for training an adaptive atrial fibrillation detector for use in in the method of FIG. 14.

Accurate detection of presence of atrial fibrillation during ECG monitoring of the ECG data segments is dependent on training accuracy. FIG. 15 is a flow diagram showing, by way of example, a routine 180 for training an adaptive atrial fibrillation detector for use in in the method 170 of FIG. 14. ECG training data, described above with reference to FIG. 3, is obtained (step 181).

The training data is divided into segments, with each segment corresponding to a temporal window during which the portion of the ECG signal in that segment was recorded (step 182). In one embodiment, the temporal window can be between 2 and 12 seconds; for example in one embodiment, the temporal window can be 8.5 seconds. Patterns of ECG features within the segments are annotated as being indicative of atrial fibrillation or not being indicative of atrial fibrillation (step 183). In one embodiment, a total of 32 unique patterns of ECG features is annotated, though other numbers of combinations are also possible.

The annotated patterns are then provided to the adaptive atrial fibrillation detector (step 184). In one embodiment, the patterns are each provided and run through the adaptive atrial fibrillation detector once. In a further embodiment, the patterns are run through the adaptive atrial fibrillation detector multiple times.

After the training data has been run through the adaptive atrial fibrillation detector, testing can be performed to determine classification accuracy of the adaptive atrial fibrillation detector (step 185). During testing, a set of testing data, such as ECG monitoring results collected by ambulatory ECG monitors, such as described above with reference to FIGS. 1-10 above, is run through the trained adaptive atrial fibrillation detector, which classifies the testing data. Additionally, the testing data is annotated manually or via a different program with classifications of being indicative of the patient experiencing atrial fibrillation at the time the data was collected or not. A comparison is made between the annotation of the data and the results of the adaptive atrial fibrillation detector. A number of samples correctly classified is determined and an average accuracy of the testing data is determined. In one embodiment, the average accuracy can be determined and reported after every n number of batches of ECG data. For example, n can represent 100 batches; however, other numbers of batches are possible. The batches can be determined based on an amount of ECG data, a number of ECG ambulatory monitors providing the data, as well as by other metrics. An accuracy threshold can be applied to the average accuracy values and if an average accuracy value or a predetermined number of average accuracy values are below the threshold, further training can be performed (block 307) to increase the accuracy of the adaptive atrial fibrillation detector.

Once the adaptive atrial fibrillation detector is accurately trained, further ECG data is collected and provided to the detector for classification. FIG. 16 is a flow diagram showing, by way of example, a routine 190 for classification of ECG data for use in the method 170 of FIG. 14 in accordance with one embodiment. The collected ECG data is divided into segments corresponding to temporal windows during which the portions of the ECG data included in the segments were collected, as described above with reference to step 182 (step 191). Optionally, noise filtering of the segments is performed prior to further processing of the segments, as further described in detail in U.S. Pat. No. 10,251,576, issued Apr. 9, 2019, entitled System And Method For ECG Data Classification For Use In Facilitating Diagnosis Of Cardiac Rhythm Disorders With The Aid Of A Digital Computer, the disclosure of which is incorporated by reference, and only non-noise ECG data segments are subjected to subsequent processing (step 192). The ECG data segments are then received by the trained adaptive atrial fibrillation detector (step 193). As described above with reference to FIG. 3, the detector can be implemented by a convolutional neural network utilizing, for example, a one dimensional formulation for use with ECG data. Additionally, the adaptive atrial fibrillation detector can include hidden layers for performing the classification. In the embodiment described below, two convolutional or pooling hidden layers, and two fully-connected hidden layers are utilized. However, other number of layers are possible.

During the first convolution layer, ECG trace features are identified (block 193) using, for example, sliding filters, though other identification techniques are possible. Examples of ECG trace features can include R waves without clearly discernible P waves, as well as other types of features that are indicative of atrial fibrillation. For example, other patterns indicative of AF can further include highly disorganized P-waves that do not settle into a repeating pattern. In one embodiment, filters for at least 32 features are run against the ECG data. During the second convolution layer, repeating patterns of the features are identified (step 194), including, for example, irregular R intervals between successive R-waves, though other patterns are possible.

Next, the data obtained from the second convolution layer is provided to a first fully connected cross-connection layer, which builds (step 195) a matrix with the repeating features representing the columns and matrix multipliers representing rows. An intersection value for each combination of the repeating features and matrix multipliers are listed in the matrix as cross connection weights. Specifically, the intersection value can be determined by multiplying each repeating feature value with a matrix multiplier and scaling the product by a predetermined factor. However, other methods for determining the intersection values are possible.

The second fully connected cross-connection layer utilizes the cross-connection weights from the first fully connected cross-connection layer and multiplies the cross-connection weights by further weights to calculate (step 196) final cross-connection values for each ECG data segment. The final cross-connection values include an atrial fibrillation classification value, which is indicative of a probability that the patient experienced atrial fibrillation during the temporal interval during which the ECG data segment was recorded, and a non-atrial fibrillation data classification value, which is indicative of the probability that the patient did not experience atrial fibrillation during the temporal period during which the ECG data segment was recorded.

Based on the final cross-connection values, a determination is made as to whether the atrial fibrillation classification value for each data segment exceeds the non-atrial fibrillation classification value (step 197). The ECG data segments for which the atrial fibrillation classification value does exceed the non-atrial fibrillation classification value are classified as associated with atrial fibrillation of the patient (step 198), signifying that the patient experienced atrial fibrillation during at least a portion of the temporal windows during which these ECG data segments were recorded. For those ECG data segments for which the atrial fibrillation classification value does not exceed the non-atrial fibrillation classification value (197), a non-atrial fibrillation classification is assigned (step 199), signifying that the patient did not experience atrial fibrillation during the temporal windows during which these ECG data segments were recorded.

While the invention has been particularly shown and described as referenced to the embodiments thereof, those skilled in the art will understand that the foregoing and other changes in form and detail may be made therein without departing from the spirit and scope.

What is claimed is:

1. A system for machine-learning-based atrial fibrillation detection with the aid of a digital computer, comprising:
   a database operable to maintain a plurality of electrocardiography (ECG) features and annotated patterns of the features, at least some of the patterns associated with atrial fibrillation;
   at least one server interconnected to the database, the at least one server configured to:
      train a classifier based on the annotated patterns in the database;
      receive a representation of an ECG signal recorded by an ambulatory monitor recorder during a plurality of temporal windows;
      detect a plurality of the ECG features in at least some of the portions of the representation falling within each of the temporal windows;

use the trained classifier to identify patterns of the ECG features within one or more of the portions of the ECG signal;

for each of the portions, calculate a value indicative of whether the portion of the representation within that ECG signal is associated the patient experiencing atrial fibrillation;

calculate a further value indicative of whether the portion of the representation within that ECG signal is associated with the patient not experiencing atrial fibrillation;

compare the further value to the value;

determine that the portion of the ECG signal is associated with the patient experiencing atrial fibrillation based on the comparison; and take an action based on the determination that the portion of the ECG signal is associated with the patient experiencing atrial fibrillation.

2. A system for machine-learning-based atrial fibrillation detection according to claim 1, the at least one server further configured to:

obtain training data comprising a plurality of the ECG features and a plurality of patterns of the ECG features; and obtain annotations of patterns of the ECG features in the training data, wherein the training of the classifier is based on the annotations.

3. A system for machine-learning-based atrial fibrillation detection according to claim 1, the at least one server further configured to:

test an accuracy of the trained classifier and perform further training based on a result of the test.

4. A system for machine-learning-based atrial fibrillation detection according to claim 1, wherein the determination is made upon the value exceeding the further value.

5. A system for machine-learning-based atrial fibrillation detection according to claim 1, wherein the action comprises sending an alert regarding the determination.

6. A system for machine-learning-based atrial fibrillation detection according to claim 1, the at least one server further configured to:

generate a matrix with the identified features and the patterns; and generate at least one matrix with weights for the identified features and patterns, wherein the value and the further value are calculated using the weight matrix.

7. A system for machine-learning-based atrial fibrillation detection according to claim 1, wherein each of the temporal windows is between 2 and 60 seconds.

8. A system for machine-learning-based atrial fibrillation detection according to claim 1, wherein the database comprises 32 of the ECG features.

9. A system for machine-learning-based atrial fibrillation detection according to claim 1, the at least one server further configured to:

perform a noise filtering of at least some of the portions of the ECG signal prior to identification of the ECG features.

10. A method for machine-learning-based atrial fibrillation detection with the aid of a digital computer, comprising:

maintaining in a database a plurality of electrocardiography (ECG) features and annotated patterns of the features, at least some of the patterns associated with atrial fibrillation;

training by an at least one server connected to the database a classifier based on the annotated patterns in the database;

receiving by the at least one server a representation of an ECG signal recorded by an ambulatory monitor recorder during a plurality of temporal windows;

detecting by the at least one server a plurality of the ECG features in at least some of the portions of the representation falling within each of the temporal windows;

using by the at least one server the trained classifier to identify patterns of the ECG features within one or more of the portions of the ECG signal;

for each of the portions, calculating by the at least one server a value indicative of whether the portion of the representation within that ECG signal is associated the patient experiencing atrial fibrillation;

calculating by the at least one server a further value indicative of whether the portion of the representation within that ECG signal is associated with the patient not experiencing atrial fibrillation;

comparing the further value to the score;

determining that the portion of the ECG signal is associated with the patient experiencing atrial fibrillation based on the comparison;

taking by the at least one server an action based on the determination that the portion of the ECG signal is associated with the patient experiencing atrial fibrillation.

11. A method for machine-learning-based atrial fibrillation detection according to claim 10, further comprising:

obtaining training data comprising a plurality of the ECG features and a plurality of patterns of the ECG features; and obtaining annotations of patterns of the ECG features in the training data, wherein the training of the classifier is based on the annotations.

12. A method for machine-learning-based atrial fibrillation detection according to claim 10, further comprising:

test an accuracy of the trained classifier and performing further training based on a result of the test.

13. A method for machine-learning-based atrial fibrillation detection according to claim 10, wherein the determination is made upon the value exceeding the further value.

14. A method for machine-learning-based atrial fibrillation detection according to claim 10, wherein the action comprises sending an alert of the regarding the determination.

15. A method for machine-learning-based atrial fibrillation detection according to claim 10, further comprising:

generating a matrix with the identified features and the patterns; and generating at least one matrix with weights for the identified features and patterns, wherein the value and the further value are calculated using the weight matrix.

16. A method for machine-learning-based atrial fibrillation detection according to claim 10, wherein each of the temporal windows is between 2 and 60 seconds.

17. A method for machine-learning-based atrial fibrillation detection according to claim 10, wherein the database comprises 32 of the ECG features.

18. A method for machine-learning-based atrial fibrillation detection according to claim 10, further comprising:

performing a noise filtering of at least some of the portions of the ECG signal prior to identification of the ECG features.

* * * * *